United States Patent [19]
Dow et al.

[11] Patent Number: 5,530,122
[45] Date of Patent: Jun. 25, 1996

[54] METHOD OF ISOLATING TEXAPHYRINS

[75] Inventors: William C. Dow, Fremont; Joan F. Carvalho, Mountain View; Miguel Rosingana, San Francisco, all of Calif.

[73] Assignee: Pharmacyclics, Inc., Sunnyvale, Calif.

[21] Appl. No.: 294,344

[22] Filed: Aug. 23, 1994

[51] Int. Cl.$^6$ .................................................. C07D 487/22
[52] U.S. Cl. ........................... 540/474; 540/470; 540/472
[58] Field of Search ..................................... 540/145, 472, 540/474, 470

[56] References Cited

U.S. PATENT DOCUMENTS

| | | | |
|---|---|---|---|
| 4,935,498 | 6/1990 | Sessler et al. | 534/15 |
| 5,252,720 | 10/1993 | Sessler et al. | 534/11 |
| 5,256,399 | 10/1993 | Sessler et al. | 424/9 |
| 5,272,142 | 12/1993 | Sessler et al. | 514/185 |
| 5,292,414 | 3/1994 | Sessler et al. | 204/157.5 |

OTHER PUBLICATIONS

Sessler et al., "Texaphyrins: Synthesis & Applications" Accounts of Chemical Research, 27 (2) 43–50, 1994.

*Primary Examiner*—Mukund J. Shah
*Assistant Examiner*—Pavanaram K. Sripada
*Attorney, Agent, or Firm*—Jacqueline S. Larson

[57] ABSTRACT

A process for the isolation of sp$^3$ reduced nonaromatic macrocyclic texaphyrin precursors, aromatic texaphyrin compounds and texaphyrin-metal complexes from aqueous salt solutions.

24 Claims, No Drawings

METHOD OF ISOLATING TEXAPHYRINS

FIELD OF THE INVENTION

This invention relates to an improved process for the isolation of nonaromatic macrocyclic compounds ("sp$^3$") which are precursors of aromatic texaphyrin compounds, and for the isolation of the aromatic texaphyrins and texaphyrin-metal complexes.

BACKGROUND OF THE INVENTION

The texaphyrins are aromatic pentadentate macrocyclic "expanded porphyrins" which have been found to be useful as MRI contrast agents, as radiosensitizers and in photodynamic therapy (PDT). Texaphyrin is considered as being an aromatic benzannulene containing both 18$\pi$- and 22$\pi$-electron delocalization pathways. See, e.g., Sessler, J. L. et al., Accounts of Chemical Research, 1994, 27, 43. Texaphyrins and water-soluble texaphyrins and method of preparation have been described in U.S. Pat. Nos. 4,935,498; 5,252,720; 5,256,399; 5,272,142; and 5,292,414; and in U.S. application Ser. No. 08/196,964; all of which are incorporated herein by reference. The aromatic free-base texaphyrins and texaphyrin metal complexes are produced by the oxidation and (for the metal complex) metallation of a reduced nonaromatic macrocycle precursor (the "sp$^3$" compound).

On an industrial scale, crystallization or precipitation are preferred methods for purification and isolation of solids such as texaphyrin-metal complexes and the nonaromatic (sp$^3$) precursors. Other techniques such as extractions do not provide texaphyrins in solid form, and chromatographic techniques are also less practical and often cost-prohibitive on a production scale.

Existing methods for texaphyrin-metal complex isolation have employed organic solvent mixtures such as heptane-ethyl acetate at ambient to slightly-elevated temperatures. Nonaromatic (sp$^3$) macrocycles have been isolated from a variety of organic solvents such as isopropanol-heptane mixtures at −23° C. (where the use of very low temperatures is cumbersome and impractical for large-scale manufacturing) or octanol at 25° C. (which requires special processing to remove the residual higher boiling solvents) or other organic solvents. For both classes of compounds, water has been avoided. The sp3 macrocycle is not stable in water, consistent with the known properties of molecules with imine bonds (the macrocycle has two such bonds). For a large number of metal-texaphyrin complexes, the water solubility of the complex precludes isolation from an aqueous system, and very poor results have been encountered with mixed aqueous-organic systems for these compounds.

The present invention addresses these deficiencies and allows aqueous-based isolation procedures to be used for these classes of compounds. Water is a highly desirable solvent due to its low cost, low toxicity, and lack of flammability. Waste disposal of aqueous materials may be expected to be preferable to organic waste streams. Another advantage of the present invention is the use of temperatures near ambient conditions, moderated by the use of ice or simple refrigeration systems. Such techniques are more practical on an industrial scale than prior techniques.

SUMMARY OF THE INVENTION

In spite of the known instability of imines and of the sp3 compound, and of the solubility of the texaphyrins, it has now been discovered by the inventors that, surprisingly, these compounds can be isolated from aqueous solutions of salts and at practical temperatures to provide a workable solid or purified material. Any texaphyrin, texaphyrin metal complex or sp$^3$ nonaromatic macrocycle may be isolated by the present process.

In particular, one embodiment of the present invention is directed to the isolation of a texaphyrin or an sp$^3$ macrocyclic precursor of a texaphyrin via precipitation from an aqueous salt solution. More particularly, the present invention provides a process for isolating a texaphyrin or an sp$^3$ nonaromatic precursor of texaphyrin, which process comprises:

(a) adding together the texaphyrin or the sp3 nonaromatic precursor and an aqueous solution of a salt at a temperature above the freezing point of the resulting reaction mixture; and (b) recovering the precipitated texaphyrin or sp3 nonaromatic precursor from the reaction mixture.

DETAILED DESCRIPTION OF THE INVENTION AND THE PREFERRED EMBODIMENTS

In the practice of the process of the present invention, the salt included in the aqueous solution may be chosen from any salt that is soluble in water or a water/organic solvent mixture and, when used with a texaphyrin metal complex, does not cause transmetallation of the texaphyrin metal complex being isolated. Preferred are those salts that are water-soluble up to at least about 10 parts by weight per 100 parts by weight of water. Salts useful in the present invention include, but are not limited to, alkali and alkaline earth metal salts; salts of the metals of group IIB; and transition metal salts. Particular anions include the halides, sulfates, bisulfates, acetates, nitrates, formates, and carbonates. Specific examples of metal salts useful in the invention are lithium, sodium, potassium, calcium, barium, magnesium, copper, zinc, and lanthanide metal salts; presently preferred are sodium chloride, sodium acetate, potassium chloride, potassium acetate, potassium bromide, potassium iodide, calcium chloride, calcium acetate, zinc chloride, and copper sulfate. Because of their particular utility in large-scale commercial (including pharmaceutical) production, most preferred are salts that have a low toxicity and are inexpensive. Examples of such preferred salts are sodium salts, such as sodium acetate and sodium chloride, and calcium salts, such as calcium acetate and calcium chloride. A single salt or a mixture of salts may be used in the practice of the invention.

The amount of salt to be used is that amount which will give a concentration of at least 0.1N up to the saturation point of the particular salt in the final reaction mixture with the texaphyrin or the sp$^3$ molecule, at the process temperature, and preferably at a salt concentration of from about 0.25 of saturation to saturation, more preferably from about 0.25 of saturation to about 0.75 of saturation in the reaction mixture. The specific amount of salt will vary depending on the particular salt chosen and the concentration of the texaphyrin or sp3 compound in solution, and can be determined without undue experimentation by methods known in the art.

The temperature at which the process of the invention is carried out will be above the freezing point of the reaction mixture of salt and texaphyrin or sp$^3$ compound in water. Usually, the temperature will be in the range of from about −10° C. to about 60° C., preferably from about −5° C. to about 40° C., and more preferably from about 0° C. to about room temperature.

The first step of the process of the invention, adding together the texaphyrin or sp³ compound and the aqueous salt solution, may be carried out in a number of ways, and the particular method of addition is not critical or controlling. Thus, for example, a dilute aqueous salt solution may be added to a concentrated texaphyrin solution, or a concentrated aqueous salt solution may be added to a dilute texaphyrin solution, or the solid salt may be added to a dilute texaphyrin solution. Alternatively, the texaphyrin solution may be added to the salt solution or the solid salt.

In certain circumstances, the inclusion of an organic co-solvent in which the salt has at least a slight solubility may be advantageous in carrying out the isolation of the texaphyrin or sp³ macrocycle product. The organic solvent is chosen from those that are miscible in water and in which the product is not soluble, and can be selected from, but not limited to, lower alcohols, such as methanol, ethanol, isopropanol, and butanol; THF; acetone; ethylene glycol dimethylether; and dioxane.

Following precipitation of the texaphyrin in the salt solution, the precipitate is recovered from the reaction mixture. The manner of recovery is not critical and can be carried out by any one of a number of methods known in the art such as filtration, centrifugation, decantation, and the like.

Following recovery of the isolated compound from the reaction mixture, the moist product may optionally be washed with a small quantity of an organic solvent which is miscible with water. Such washing removes trace impurities, residual water and residual salt and is useful to facilitate drying, particularly with large volumes of product such as are encountered in large, industrial scale production.

The texaphyrins and the sp³ compounds are known in the art and are disclosed in the U.S. patents and patent applications previously incorporated by reference herein.

Representatives of the sp³ nonaromatic precursor of texaphyrin are included within the following formula (A):

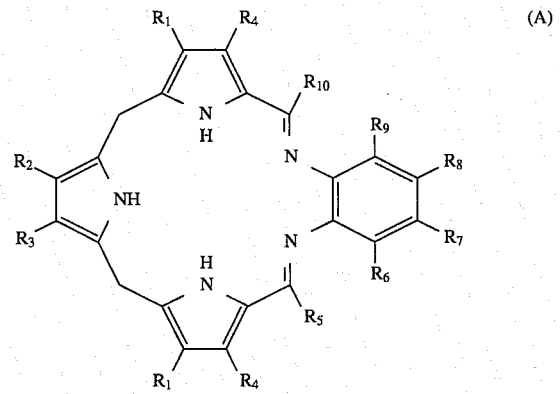

wherein, each of $R_1$–$R_4$ and $R_6$–$R_9$ is independently hydrogen, halide other than iodide, hydroxyl, alkyl, aryl, haloalkyl other than iodoalkyl, nitro, formyl, acyl, hydroxyalkyl, oxyalkyl, oxyhydroxyalkyl, saccharide, aminoalkyl, oxyaminoalkyl, carboxy, carboxyalkyl, carboxyalkoxy, hydoalkoxy, or carboxyamidealkyl; and each of $R_5$ and $R_{10}$ is independently hydrogen, alkyl, aryl, hydroxyalkyl, oxyalkyl, oxyhydroxyalkyl, aminoalkyl, oxyaminoalkyl, carboxyalkyl, carboxyalkoxy, hydoxyalkoxy, or carboxyamidealkyl.

Representatives of texaphyrin are included within the following formula (B):

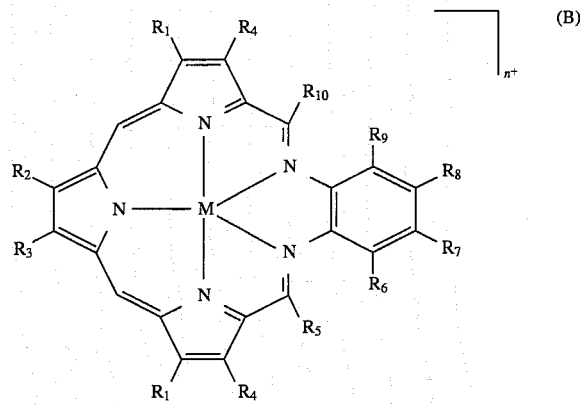

wherein, M is hydrogen, a divalent metal cation or a trivalent metal cation; each of $R_1$–$R_4$ and $R_6$–$R_9$ is independently hydrogen, halide other than iodide, hydroxyl, alkyl, aryl, haloalkyl other than iodoalkyl, nitro, formyl, acyl, hydroxyalkyl, oxyalkyl, oxyhydroxyalkyl, saccharide, aminoalkyl, oxyaminoalkyl, carboxy, carboxyalkyl, carboxyalkoxy, hydoxyalkoxy, or carboxyamidealkyl; each of $R_5$ and $R_{10}$ is independently hydrogen, alkyl, aryl, hydroxyalkyl, oxyalkyl, oxyhydroxyalkyl, aminoalkyl, oxyaminoalkyl, carboxyalkyl, carboxyalkoxy, hydoxyalkoxy, or carboxyamidealkyl; and n is 0, 1 or 2.

In the practice of the present invention, presently preferred compounds are those of formula (A) or (B) where $R_1$ is hydroxyalkyl; $R_2$, $R_3$, and $R_4$ are alkyls; $R_5$, $R_6$, $R_9$, and $R_{10}$ are hydrogen; $R_7$ and $R_8$ are independently hydrogen, hydroxyalkyl, carboxyalkyl or oxyalkyl; and, for formula (B), M is a lanthanide metal cation. More preferred are the compounds where M is Gd(III), Lu(III), Eu(III) or Dy(III); $R_1$ is 3-hydroxypropyl; $R_2$ and $R_3$ are ethyl; $R_4$ is methyl; $R_5$, $R_6$, $R_9$, and $R_{10}$ are hydrogen; and $R_7$ and $R_8$ are both —O(CH$_2$)$_3$OH or —O(CH$_2$CH$_2$O)$_3$CH$_3$, or $R_7$ is hydrogen and $R_8$ is —O(CH$_2$)$_n$COOH where n is 1–3. However, while the above are presently preferred compounds which can be isolated by the present invention, the invention is not limited thereto and any texaphyrin, texaphyrin metal complex or sp³ nonaromatic macrocycle may be isolated by the present process.

The following examples are provided to illustrate the practice of the present invention, and are intended neither to define nor to limit the scope of the invention in any manner. "RT" means room temperature.

EXAMPLE 1

The sp³ macrocyclic compound 4,5-diethyl-10,23-dimethyl-9,24-bis(3-hydroxypropyl)-16,17-bis[2-[2-(2-methoxyethoxy)ethoxy]ethoxy]-13,20,25,26,27-pentaazapentacyclo(20.2.1.1$^{3,6}$.1$^{8,11}$.0$^{14,19}$)heptacosa- 3,5,8,10,12,14 (19), 15,178,20,22,24 -undecaene [the compound of formula (A) where $R_1$ is 3-hydroxypropyl; $R_2$ and $R_3$ are ethyl; $R_4$ is methyl; $R_5$, $R_6$, $R_9$, and $R_{10}$ are hydrogen; and $R_7$ and $R_8$ are —O(CH$_2$CH$_2$O)$_3$CH$_3$] was isolated by precipitation from water by the addition of sodium acetate as follows.

The sp³ hydrochloride salt was prepared by condensation of the diformyltripyrrole 2,5-bis[(5-formyl-3-hydroxypropyl-4-methylpyrrol-2-yl)methyl]-3,4-diethylpyrrole and the ortho-phenylenediamine 1,2-diamino-4,5-bis[2-[2-(2-methoxyethoxy)ethoxy]ethoxy]benzene by methods disclosed in the art, e.g. in the U.S. patents incorporated herein by reference. The resulting HCl salt of the sp$^3$ compound (700 mg) was dissolved in 10.5 mL water and stirred for 70 min at RT, pH=2.0. The solution was then cooled to 0° C. for 15 min, after which 5.25 mL of 10N sodium acetate was added and the resulting mixture was stirred for 1 hr at 0° C., pH=6.7. The precipitate that formed was collected at 0° C. by filtration and dried to give the purified sp$^3$ compound. The weight of the recovered compound was 704 mg. For the above sp$^3$ compound.0.9NaOAc.0.2HCl calculated, C=62.44, H=7.6, N=7.3, Cl=0.7, Na=2.16; found, C=61.27, H=7.71, N=6.94, Cl=0.67, Na=2.13.

EXAMPLE 2

The sp$^3$ nonaromatic macrocycle 4,5-diethyl-10,23-dimethyl-9,24-bis(3 -hydroxypropyl)-16,17-bis[2-[2-(2-methoxyethoxy)ethoxy]ethoxy]-13,20,25,26,27 -pentaazapentacyclo(20.2.1.1$^{3,6}$.1$^{8,11}$.0$^{14,19}$)heptacosa-3,5,8,10,12,14(19), 15,17,20,22,24 -undecaene was isolated by precipitation from water by the addition of sodium chloride as follows.

The hydrochloride salt of the above sp$^3$ compound (750 mg) was dissolved in 12.0 mL of water and stirred for 1 hr at RT, pH=1.87. The solution was then cooled to 0° C., after which 12.0 mL of saturated sodium chloride was added over 40 min. The resulting suspension was stirred for 1 hr at 0° C., pH=1.90. The suspension was centrifuged at 0° C. for 30 min at 4000 rpm, the resulting solution was decanted and the wet precipitate was dried to give the purified sp$^3$ compound in essentially quantitative yield.

EXAMPLE 3

Following the procedures of Example 1 or 2, the sp$^3$ compound 4,5-diethyl-10,23 -dimethyl-9,24-bis(3-hydroxypropyl)-16,17-bis(3-hydroxypropyl-1-oxy)-13,20,25,26,27 -pentaazapentacyclo(20.2.1.1$^{3,6}$.1$^{8,11}$.0$^{14,19}$)heptacosa-3,5, 8,10,12,14(19),15,178,20,22,24 -undecaene [the compound of formula (A) where $R_1$ is 3-hydroxypropyl; $R_2$ and $R_3$ are ethyl; $R_4$ is methyl; $R_5$, $R_6$, $R_9$, and $R_{10}$ are hydrogen; and $R_7$ and $R_8$ are —OCH$_2$CH$_2$CH$_2$OH] is isolated by precipitation from water by the addition of an aqueous salt solution.

EXAMPLE 4

The gadolinium(III) metal complex of 4,5-diethyl-10,23-dimethyl-9,24-bis(3 -hydroxypropyl)-16,17-bis[2-[2-(2-methoxyethoxy)ethoxy]ethoxy]-13,20,25,26,27 -pentaazapentacyclo(20.2.1.1$^{3,6}$.1$^{8,11}$.0$^{14,19}$)heptacosa-1,3,5,7,9, 11(27), 12,14(19),15,17,20,22(25),23-undecaene [the compound of formula (B) where M is Gd(III), $R_1$ is 3-hydroxypropyl; $R_2$ and $R_3$ are ethyl; $R_4$ is methyl; $R_5$, $R_6$, $R_9$, and $R_{10}$ are hydrogen; and $R_7$ and $R_8$ are —O(CH$_2$CH$_2$O)$_3$CH$_3$] was isolated from water as follows.

The Gd(III) metal complex of the texaphyrin was prepared by oxidation of the sp$^3$ macrocycle precursor from Example 1 or 2, followed by metallation with a Gd salt such as gadolinium(III) acetate tetrahydrate by methods disclosed in the art, e.g. in the U.S. patents previously incorporated by reference herein. The metal complex product (1 mL, 20 mg/mL) was added dropwise to 4 mL of saturated sodium acetate at RT. A green precipitate appeared almost immediately upon addition. The precipitate was collected by filtration and dried under vacuum to give the final Gd(III) texaphyrin product.

EXAMPLE 5

The gadolinium(III) metal complex of 4,5-diethyl-10,23-dimethyl-9,24-bis(3 -hydroxypropyl)-16,17-bis[2-[2-(2-methoxyethoxy)ethoxy]ethoxy]-13,20,25,26,27 -pentaazapentacyclo(20.2.1.1$^{3,6}$.1$^{8,11}$.0$^{14,19}$)heptacosa-1,3,5,7,9,11(27), 12,14(19),15,17,20,22(25),23-undecaene was isolated from water as follows.

A 20 mg/mL solution of the Gd(III) metal complex of the texaphyrin was layered over a saturated solution of sodium acetate, 4 mL, at RT. A green precipitate appeared within minutes. The precipitate was collected by filtration and dried under vacuum to give the final Gd(III) texaphyrin product.

EXAMPLE 6

The gadolinium(III) metal complex of 4,5-diethyl-10,23-dimethyl-9,24-bis(3 -hydroxypropyl)-16,17-bis[2-[2-(2-methoxyethoxy)ethoxy]ethoxy]-13,20,25,26,27 -pentaazapentacyclo(20.2.1.1$^{3,6}$.1$^{8,11}$.0$^{14,19}$)heptacosa-1,3,5,7,9,11(27), 12,14(19),15,17,20,22(25),23-undecaene was isolated from a non-saturated aqueous salt solution as follows.

Five drops of a 5 mg/mL solution of the Gd(III) metal complex of the texaphyrin was layered over 4 mL of a half-saturated (ca. 7M) solution of sodium acetate at RT. A green precipitate appeared within minutes. The precipitate was collected by filtration and dried under vacuum to give the final Gd(III) texaphyrin product.

EXAMPLE 7

Following the procedures of Example 4, 5 or 6, the lutetium(III) metal complex of 4,5-diethyl-10,23-dimethyl-9,24-bis(3-hydroxypropyl)-16,17-bis[2-[2=(2 -methoxyethoxy)ethoxy]-ethoxy]-13,20,25,26,27 -pentaazapentacyclo(20.2.1.1$^{3,6}$.1$^{8,11}$.0$^{14,19}$)heptacosa- 1,3,5,7,9,11(27), 12,14(19),15,17,20,22(25),23-undecaene is isolated from a sodium acetate salt solution.

In the same manner, the gadolinium(III) metal complex and the lutetium(III) metal complex of 4,5-diethyl-10,23-dimethyl-9,24-bis(3-hydroxypropyl)-16,17-bis(3 -hydroxypropyl-1-oxy)-13,20,25,26,27-pentaazapentacyclo(20.2.1.1$^{3,6}$.1$^{8,11}$ .0$^{14,19}$)heptacosa-1,3,5,7,9,11(27), 12,14(19),15,17,20,22(25),23-undecaene are each isolated from a sodium acetate salt solution.

This invention has been described in detail with particular reference to certain preferred embodiments thereof, but it will be understood that variations and modifications can be effected within the spirit and scope of the invention.

What is claimed is:

1. A process for isolating an sp$^3$ reduced nonaromatic macrocycle, the process comprising:

(a) adding together the sp$^3$ nonaromatic macrocycle and an aqueous solution of a salt at a temperature above the freezing point of the resulting reaction mixture; and (b) recovering the precipitated sp$^3$ nonaromatic macrocycle from the reaction mixture.

2. A process according to claim 1 wherein the sp$^3$ nonaromatic macrocycle is of the following formula (A):

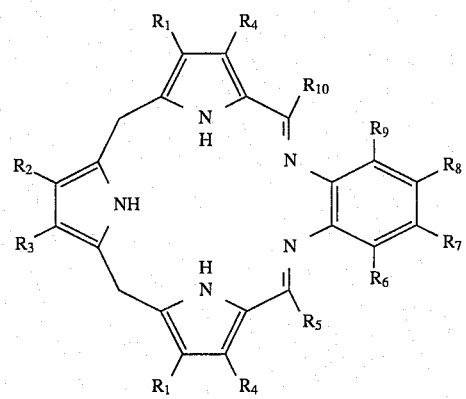

(A)

wherein, each of $R_1$–$R_4$ and $R_6$–$R_9$ is independently hydrogen, halide other than iodide, hydroxyl, alkyl, aryl, haloalkyl other than iodoalkyl, nitro, formyl, acyl, hydroxyalkyl, oxyalkyl, oxyhydroxyalkyl, saccharide, aminoalkyl, oxyaminoalkyl, carboxy, carboxyalkyl, carboxyalkoxy, hydoxyalkoxy, or carboxyamidealkyl; and each of $R_5$ and $R_{10}$ is independently hydrogen, alkyl, aryl, hydroxyalkyl, oxyalkyl, oxyhydroxyalkyl, aminoalkyl, oxyaminoalkyl, carboxyalkyl, carboxyalkoxy, hydoxyalkoxy, or carboxyamidealkyl.

3. A process according to claim 1 wherein the temperature is from about –10° C. to about 60° C.

4. A process according to claim 1 wherein the temperature is from about –5° C. to about 40° C.

5. A process according to claim 1 wherein the temperature is from about 0° C. to about room temperature.

6. A process according to claim 1 wherein the salt is a metal salt.

7. A process according to claim 1 wherein the salt is an alkali metal salt or an alkaline earth metal salt.

8. A process according to claim 1 wherein the salt is a halide, a sulfate, a bisulfate, an acetate, a nitrate, a formate, or a carbonate.

9. A process according to claim 1 wherein the salt is a sodium salt or a calcium salt.

10. A process according to claim 2 wherein $R_1$ is hydroxyalkyl; $R_2$, $R_3$, and $R_4$ are alkyls; $R_5$, $R_6$, $R_9$, and $R_{10}$ are hydrogen; and $R_7$ and $R_8$ are independently hydrogen, hydroxyalkyl, carboxyalkyl, carboxyalkoxy, hydoxyalkoxy, or oxyalkyl.

11. A process according to claim 2 wherein $R_1$ is 3-hydroxypropyl; $R_2$ and $R_3$ are ethyl; $R_4$ is methyl; $R_5$, $R_6$, $R_9$, and $R_{10}$ are hydrogen; and $R_7$ and $R_8$ are both —O(CH$_2$)$_3$OH or —O(CH$_2$CH$_2$O)$_3$CH$_3$, or $R_7$ is hydrogen and $R_8$ is —O(CH$_2$)$_n$COOH where n is 1–3.

12. A process according to claim 1 wherein the process further comprises a step of washing the recovered sp$^3$ nonaromatic macrocycle with an organic solvent that is miscible with water and in which the sp$^3$ nonaromatic macrocycle is not soluble.

13. A process for isolating a texaphyrin, the process comprising:
   (a) adding together the texaphyrin and an aqueous solution of a salt at a temperature above the freezing point of the resulting reaction mixture; and
   (b) recovering the precipitated texaphyrin from the reaction mixture.

14. A process according to claim 13 wherein the texaphyrin is of the following formula (B):

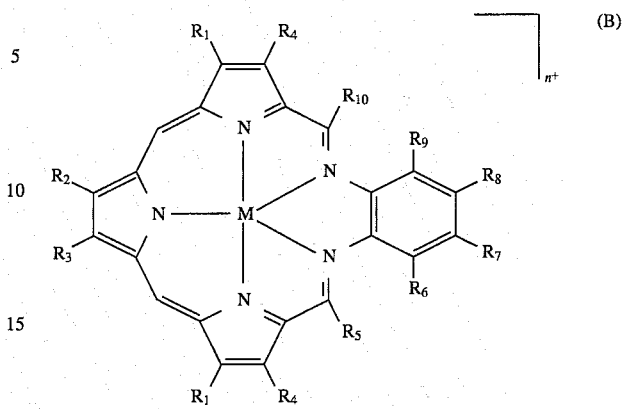

(B)

wherein, M is H, a divalent metal cation or a trivalent metal cation; each of $R_1$–$R_4$ and $R_6$–$R_9$ is independently hydrogen, halide other than iodide, hydroxyl, alkyl, aryl, haloalkyl other than iodoalkyl, nitro, formyl, acyl, hydroxyalkyl, oxyalkyl, oxyhydroxyalkyl, saccharide, aminoalkyl, oxyaminoalkyl, carboxy, carboxyalkyl, carboxyalkoxy, hydoxalkoxy, or carboxyamidealkyl; each of $R_5$ and $R_{10}$ is independently hydrogen, alkyl, aryl, hydroxyalkyl, oxyalkyl, oxyhydroxyalkyl, aminoalkyl, oxyaminoalkyl, carboxyalkyl, carboxyalkoxy, hydoxalkoxy, or carboxyamidealkyl; and n is 0, 1 or 2.

15. A process according to claim 13 wherein the temperature is from about –10° C. to about 60° C.

16. A process according to claim 13 wherein the temperature is from about –5° C. to about 40° C.

17. A process according to claim 13 wherein the temperature is from about 0° C. to about room temperature.

18. A process according to claim 13 wherein the salt is a metal salt.

19. A process according to claim 13 wherein the salt is an alkali metal salt or an alkaline earth metal salt.

20. A process according to claim 13 wherein the salt is a halide, a sulfate, a bisulfate, an acetate, a nitrate, a formate, or a carbonate.

21. A process according to claim 13 wherein the salt is a sodium salt or a calcium salt.

22. A process according to claim 14 wherein $R_1$ is hydroxyalkyl; M is a lanthanide metal cation; $R_2$, $R_3$, and $R_4$ are alkyls; $R_5$, $R_6$, $R_9$, and $R_{10}$ are hydrogen; and $R_7$ and $R_8$ are independently hydrogen, hydroxyalkyl, carboxyalkyl, carboxyalkoxy, hydoxalkoxy, or oxyalkyl.

23. A process according to claim 14 wherein M is Gd(III), Lu(III), Eu(III) or Dy(III); $R_1$ is 3-hydroxypropyl; $R_2$ and $R_3$ are ethyl; $R_4$ is methyl; $R_5$, $R_6$, $R_9$, and $R_{10}$ are hydrogen; and $R_7$ and $R_8$ are both —O(CH$_2$)$_3$OH or —O(CH$_2$CH$_2$O)$_3$CH$_3$, or $R_7$ is hydrogen and $R_8$ is —O(CH$_2$)$_n$COOH where n is 1–3.

24. A process according to claim 13 wherein the process further comprises a step of washing the recovered texaphyrin with an organic solvent that is miscible with water and in which the texaphyrin is not soluble.

\* \* \* \* \*